US009101367B2

(12) United States Patent
Stammberger (10) Patent No.: US 9,101,367 B2
(45) Date of Patent: Aug. 11, 2015

(54) MEDICAL INSTRUMENT FOR DISSECTING TISSUE (75) Inventor: Heinz Stammberger, Graz (AT)

(73) Assignee: KARL STORZ GMBH & CO. KG (DE)

(*) Notice: Subject to any disclaimer, the term of this patent is extended or adjusted under 35 U.S.C. 154(b) by 2141 days.

(21) Appl. No.: 11/219,574

(22) Filed: Sep. 2, 2005

(65) Prior Publication Data

US 2006/0052808 A1 Mar. 9, 2006

Related U.S. Application Data (63) Continuation of application No. PCT/EP2004/009915, filed on Sep. 6, 2004.

(30) Foreign Application Priority Data

Sep. 5, 2003 (DE) .................................. 103 42 002

(51) Int. Cl.
A61B 17/32 (2006.01)
A61B 17/16 (2006.01)
A61B 17/3205 (2006.01)
A61B 17/24 (2006.01)
A61B 10/04 (2006.01)

(52) U.S. Cl.
CPC ......... *A61B 17/1611* (2013.01); *A61B 17/1688* (2013.01); *A61B 17/24* (2013.01); *A61B 17/32* (2013.01); *A61B 17/32053* (2013.01); *A61B 10/04* (2013.01); *A61B 17/1679* (2013.01)

(58) Field of Classification Search
CPC .... A61B 10/04; A61B 17/1611; A61B 17/24; A61B 17/32; A61B 17/32053

USPC ......... 606/159, 167, 170, 171, 184, 205, 207; 600/564, 566, 567; 30/134, 342
See application file for complete search history.

(56) References Cited

U.S. PATENT DOCUMENTS

| 1,167,014 A | * | 1/1916 | O-Brien | 606/151 |
| 2,505,358 A | * | 4/1950 | Gusberg et al. | 600/564 |
| 3,705,577 A | * | 12/1972 | Sierra | 600/567 |

(Continued)

FOREIGN PATENT DOCUMENTS

| DE | 849 592 | 9/1952 |
| DE | 67 204 | 6/1969 |

(Continued)

OTHER PUBLICATIONS

International Preliminary Report; Mar. 6, 2006; 5 pages.

(Continued)

*Primary Examiner* — Thomas McEvoy
*Assistant Examiner* — Julie A Szpira
(74) *Attorney, Agent, or Firm* — Whitmyer IP Group LLC (57) ABSTRACT A medical instrument for dissecting human and/or animal tissue comprises a shaft, a first tool and a second tool at a distal end of the shaft, the first tool and the second tool cooperating in the manner of a punch by means of an axial relative movement with respect to one another, and at least one of the tools comprising a cutting element which is arranged in such a way that it forms, with the other tool, a punch area that defines a plane which, with a longitudinal axis of the shaft, forms an angle in the area of the distal end of the shaft. The distally arranged tool tapers convexly in diameter toward the distal end in the longitudinal direction of the shaft, the external contour lines of the distally arranged tool intersecting, when viewed in a section through a longitudinal central plane, at an angle smaller than 160°.

24 Claims, 6 Drawing Sheets

(56) References Cited

U.S. PATENT DOCUMENTS

| | | | |
|---|---|---|---|
| 3,837,345 A * | 9/1974 | Matar | 606/159 |
| 5,085,659 A * | 2/1992 | Rydell | 606/47 |
| 5,171,255 A * | 12/1992 | Rydell | 606/170 |
| 5,582,618 A | 12/1996 | Chin et al. | 606/170 |
| 5,766,177 A | 6/1998 | Lucas-Dean et al. | 606/83 |
| 6,500,189 B1 | 12/2002 | Lang et al. | 606/170 |
| 2002/0143354 A1 | 10/2002 | Lang | 606/167 |

FOREIGN PATENT DOCUMENTS

| | | |
|---|---|---|
| DE | 29506466 U1 | 7/1995 |
| EP | 0 614 647 | 9/1994 |
| EP | 1 055 397 | 11/2000 |
| GB | 2 198 950 | 6/1988 |

OTHER PUBLICATIONS

PCT International Search Report, Jan. 5, 2005, 3 pages.
Endoscopes and instruments for ENT, 6$^{th}$ edition, Jan. 2000, from Karl Storz GmbH & Co. KG., 2 pages.
International Preliminary Report on Patentability & Translation of Written Opinion of the International Searching Authority, Jul. 10, 2006, 6 pages.
German Office Action; Application No. 103 42 002.9-35; Jul. 9, 2010; 3 pages.

* cited by examiner

MEDICAL INSTRUMENT FOR DISSECTING TISSUE

CROSS REFERENCE TO RELATED APPLICATIONS

The present application is a continuation of pending International patent application PCT/EP2004/009915 filed on Sep. 6, 2004 which designates the United States and which claims priority of German patent application 103 42 002.9 filed on Sep. 5, 2003.

BACKGROUND OF THE INVENTION

The present invention generally relates to the field of medical instruments for dissecting human and/or animal tissue.

Such an instrument is known, for example, under order numbers 651050, 651055, 651060 or 651065 from the German catalog "Endoskope und Instrumente für HNO" [Endoscopes and instruments for ENT], 6th edition, Janurary/2000, from Karl Storz GmbH & Co. KG.

The instrument for dissecting tissue is an instrument for detachment of tissue, for example of hard tissue and/or bone, in particular a tissue punch.

Surgical instruments of this kind are used in the context of minimally invasive surgery for detaching hard tissue or bone in the human or animal body, usually under endoscopic visual control. For this purpose, instruments of this kind have an elongate shaft at whose distal end at least one movable tool is arranged which interacts with another movable or immovable tool at the distal end of the shaft in order to detach tissue.

Surgical instruments whose tools cooperate with one another on the basis of an axial relative movement have the advantage that the effective diameter of the instrument does not change upon opening and closing of the tools. As a result, damage to the surrounding tissue or surrounding bone by opening and closing of the tools is avoided.

By virtue of the fact that the effective diameter of the instrument does not increase upon opening and closing of the tools, such instruments can also be used in smaller body apertures than can those instruments which have tools opening like forceps.

Such tissue punches are therefore preferably used in ear, nose and throat surgery (ENT surgery) in which the smaller effective diameter of the instrument is of great advantage.

Such instruments have a shaft at whose distal end two tools are arranged. Of these two tools, at least one is axially movable relative to the second tool. In the known instrument, at least one of these two tools has an approximately circular cutting element on the side facing toward the second tool. By means of their axial relative movement with respect to one another, the two tools act in the manner of a punch. In this case, the at least one cutting element defines a punch area which is approximately at right angles to the longitudinal axis of the shaft in the distal area thereof.

During use of these instruments, however, it has been shown that high loads can occur in small areas of the cutting elements of the instrument, especially when cutting through bone lamellae which are at an angle to the punch area. It has been found that this can lead to damage of the cutting surfaces or even to breaking-off of metal pieces from the cutting elements. These metal parts that have broken off are extremely sharp-edged and remain in the patient's body. These metal pieces left behind may migrate through the tissue and may cause not inconsiderable damage there. This is extremely dangerous for the patient, especially in the area of ENT surgery.

The operational safety of the known instruments is thus not guaranteed.

The patent specification U.S. Pat. No. 5,582,618 discloses a surgical instrument with a shaft at whose distal end two tools are arranged, of which one tool is axially displaceable relative to the second tool. These two tools each have a straight cutting element on an upper edge. A straight punch line is defined by these cutting elements.

The disadvantage of these instruments is that they only permit cutting along a straight punch line. Cutting about a partial circle, as is possible with the above-described instruments and as is desirable especially in ENT surgery, is not possible with such an instrument.

When an instrument of the type specified in the introduction is to be used for punching of bone lamellae, as is the case without limiting the general application of the instrument of the present invention, it is necessary first to push the distally arranged tools of the instrument through the bone lamella until the punch area comes to lie in the area of the bone lamella. The previously known instruments are not suitable for cutting through bone lamellae.

SUMMARY OF THE INVENTION

It is therefore an object of the present invention to make available a surgical instrument of the type specified in the introduction which is improved in terms of its suitability for punching of bone lamellae.

According to an aspect of the present invention, a medical instrument for dissecting tissue is provided, comprising a shaft having a longitudinal axis and a distal end, a first tool and a second tool both arranged at said distal end of said shaft, said first tool being arranged distally from said second tool, said first and second tools cooperating in the manner of a punch by an axial relative movement with respect to one another, at least one of said first and second tools comprising a cutting element arranged in such a way that said cutting element forms a punch area with the other of said first and second tools, said punch area defining a plane which forms a first angle with said longitudinal axis of said shaft which is different than 0° in the area of said distal end of said shaft, said distally arranged first tool tapering in diameter convexly in distal direction, external contour lines of said distally arranged first tool intersecting, when viewed in a section through a longitudinal central plane, at a second angle smaller than 160°.

With this configuration of the distally arranged tool of the instrument according to the invention, the instrument is suitable in particular for punching of bone lamellae, because the instrument, with its distally arranged tool leading, can first penetrate through the bone lamella until the punch area of the two tools, which lies farther in the proximal direction, comes to lie on the bone lamella. Penetration of the bone lamellae is made easier in this way, because the distally arranged tool, which has to penetrate the bone lamella, runs to a point at the distal end. With this geometry of the distally arranged tool, undesired breaking-off of the bone lamella at a site other than the punch position is avoided.

In preferred embodiments, the aforementioned angle is smaller than 140°, in particular smaller than 120°, and more particularly smaller than 100°, but preferably greater than 50°.

Although it is possible for the outermost distal end of the distally arranged tool, while still being relatively pointed, to be nonetheless cut perpendicular to the longitudinal axis of the shaft or rounded, it is further preferred if the external contour lines run together to a point.

The advantage of this is that the distally arranged tool can be placed with spot precision on the bone lamella prior to penetration of said bone lamella, the distally arranged tool thus serving as a bore sight aid for the instrument. The aforementioned point can also preferably be rounded with a very small radius in order to avoid unwanted tissue trauma.

In a further preferred embodiment, the convex portion of the distally arranged tool merges into a straight portion extending at least approximately parallel to the longitudinal axis of the shaft.

The advantage of this is that an excessive increase in diameter of the distally arranged tool in its proximal area is avoided, so that the tools retain what is overall a very slender diameter, although the greatest possible punch area is created by the two tools.

In a further preferred embodiment, the proximally arranged tool has a smaller external diameter than a proximal end of the distally arranged tool, such that the proximally arranged tool engages into the distally arranged tool during punching.

This measure too is especially advantageous if, before the punching procedure, the distally arranged tool has to be pushed through the tissue that is to be punched. By virtue of the smaller diameter of the proximally arranged tool, the latter does not create an obstacle on which the tissue can catch as the instrument is being advanced through the tissue to be penetrated. Instead, the tissue then slides over the proximal end of the distally arranged tool, so that the two tools can be brought effortlessly into the position, relative to the tissue, required for the punching procedure.

In a further preferred embodiment, the angle between the longitudinal axis of the shaft, in the area of the distal end of the shaft, and the plane defined by the punch area is different than 90°.

It has been shown that, by angling the punch area relative to the longitudinal axis of the shaft, it is possible to create a greater contact surface between the cutting elements and the bone lamellae that are to be cut through. By increasing this contact surface, the loading of the cutting elements of the tools relative to the surface is reduced. In this way, bone lamellae can be cut through much more effectively, and the medical instrument is exposed to much less wear and fatigue. The operational safety is improved in this way, since the danger of tool parts breaking off is reduced.

In a further preferred embodiment, the angle between the longitudinal axis of the shaft, in the area of the distal end of the shaft, and the plane defined by the punch area lies between approximately 20° and approximately 80°, and more preferably between approximately 30° and approximately 70°.

It has been shown that most bone lamellae to be cut through, especially in the field of ENT surgery, are found at approximately this angle with respect to the longitudinal axis of the shaft of the medical instrument. Bone lamellae at an angle of approximately 45° are especially common, although angles of approximately 65° are also found in the area of the frontal sinus.

The more the angle between the plane defined by the punch area and the longitudinal axis of the distal end of the shaft is adapted to the profile of the bone lamella, the greater the contact surface with which the cutting elements bear on the bone lamella, and the smaller the load exerted on these cutting elements.

In a further preferred embodiment, the plane defined by the punch area extends either from top-proximal to bottom-distal, from top-distal to bottom-proximal, from right-proximal to left-distal, or from right-distal to left-proximal.

These different orientations of the punch area in the four spatial directions are important especially for instruments which have a curve in the distal portion, because, in these instruments, orientation of the punch area is difficult, or impossible, by simple turning of the shaft.

The orientation of the punch area in one of the four spatial directions also greatly facilitates the use of a medical instrument according to the invention, because the orientation of the punch area in relation to a grip part mounted at the proximal end of the shaft is readily discernible to the operating surgeon.

In a further preferred embodiment, the cutting element is designed about a complete circumference on the first or second tool.

This embodiment has the advantage that the complete circumference of the tools can used for making a cut, without the shaft having to be turned for this purpose. The handling of the instrument is improved in this way. This is especially important for instruments which have a curve in the distal portion of the shaft, because, in these instruments, orientation of the punch area is difficult, or impossible, by simple turning of the shaft.

In a further preferred embodiment, the tools have an approximately circular cross section.

An approximately circular cross section of the tools is advantageous since the tools then have no corners or edges which, during insertion or removal or during the intervention itself, may cause unwanted damage to the patient's bones or tissues.

An approximately circular cross section also has the advantage that an ellipsoid or circular cutting element can be formed about the complete circumference on the tool.

In a further preferred embodiment, the diameter of the tools lies in the range from approximately 2 mm to approximately 8 mm, particularly preferably in the range from approximately 3 mm to approximately 5 mm.

These abovementioned sizes are advantageously suitable for use of the instruments in minimally invasive surgery, especially in minimally invasive ENT surgery.

In a further preferred embodiment, the first tool and the second tool, in the closed position, form a ball-shaped or a double paraboloid or ellipsoid profile, in particular an egg-shaped, tear-shaped or lobe-shaped profile.

It has been found that the above-described profiles for the tools greatly facilitate the insertion of the instrument at the operating site. By virtue of the rounded, tapering distal end of the tool arrangement, it is especially easy to guide the instrument through small openings. By virtue of the tapering at the proximal end of the tools, removal of the instrument from the body cavity is in turn made much easier.

In a further preferred embodiment, the first tool is movable and the second tool is immovable, and the second tool is arranged to the distal side of the first tool.

By means of this arrangement, the distal end of the instrument is not displaced during the punching procedure; this facilitates the positioning of the tools and also reduces the danger of damage to surrounding tissue caused by the distal end of the instrument moving when the tools are actuated.

In a further preferred embodiment, the first tool is secured against turning relative to the second tool.

This configuration is especially advantageous because it ensures that the cutting elements of the two tools are at all times able to interact optimally with one another, which is particularly important with an ellipsoid configuration of the cutting elements, since in this case there is no symmetry of rotation of the cutting elements.

In a further preferred embodiment, both tools have cutting elements.

The provision of cutting elements on both tools results in much more efficient cutting compared to an instrument in which only one tool has a cutting element and the other acts as an "anvil" for the punch.

In a further preferred embodiment, the shaft has at least one curve.

This is advantageous, particularly in surgical interventions in the ENT area, for being able to bring the tools at the distal end of the shaft to difficultly accessible locations, e.g. niches in the frontal sinus or maxillary sinus.

In a further preferred embodiment, the curve of the shaft has an angle of curvature in the range from approximately 20° to approximately 90°, and more preferably in the range from approximately 45° to approximately 65°.

These angles have proven particularly suitable for reaching the abovementioned difficultly accessible areas in ENT surgery.

It will be appreciated that the features mentioned above, and those still to be explained below, may be used not only in the respectively cited combination but also in other combinations or singly, without departing from the scope of the present invention.

BRIEF DESCRIPTION OF THE DRAWINGS

Illustrative embodiments of the invention are explained in greater detail in the following description and are depicted in the drawings, in which.

DETAILED DESCRIPTION OF PREFERRED EMBODIMENTS

Figure 1:
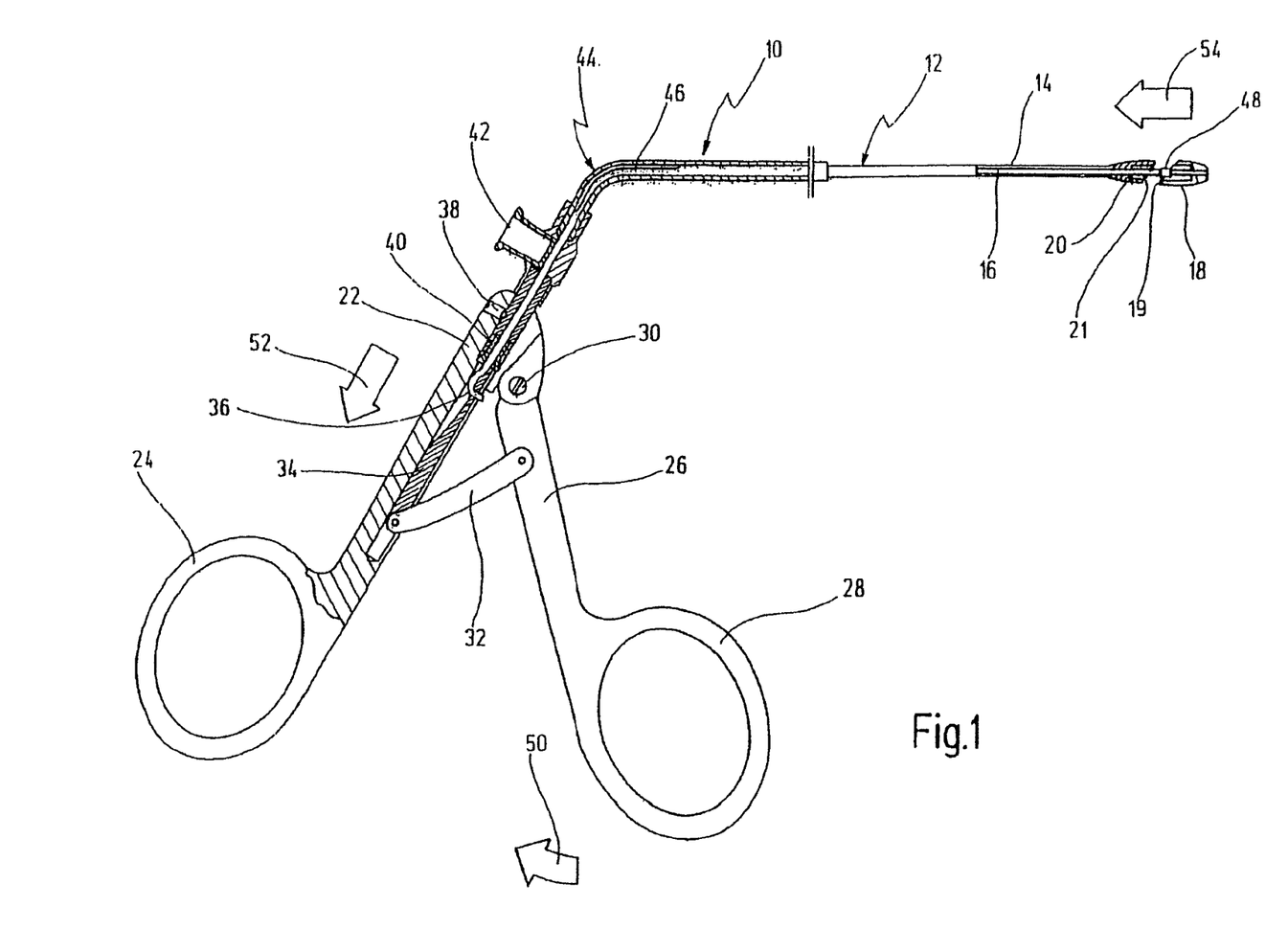
FIG. 1 shows, in a partially sectioned side view, an illustrative embodiment of a medical instrument according to the invention with the tools in the open position.

In FIG. 1, a medical instrument for dissecting human and/or animal tissue is designated by general reference number 10.

The instrument 10 according to the invention has a shaft 12. The shaft 12 is formed by a tubular element 14 in which a force transmission element 16 extends. Along the greater part of its length, the force transmission element 16 has a cross section in the shape of a triangle. In this way, irrigation channels for an irrigation liquid are formed between the force transmission element 16 and the tubular element 14.

Arranged at the distal end of the shaft 12 there is a first tool 18 which, at its proximal end, has an ellipsoid cutting element 19 about the complete circumference. The first tool 18 is connected fixedly to the force transmission element 16, for example by laser welding, and is axially movable relative to the shaft 12. In the proximal direction from the first tool 18, a second tool 20 is arranged at the distal end of the shaft 12, which second tool 20 has, at its distal end, an ellipsoid cutting element 21 about the complete circumference. The second tool 20 is in this case connected immovably to the tubular element 14.

The cutting elements 19 and 21 are arranged in such a way that, when the tools are closed, the cutting element 19 extends past the outside of the cutting element 21, and the cutting element 21 engages in the tool 18.

A first grip part 22 is arranged at the proximal end of the shaft 12.

This grip part 22 is designed in the form of a scissor grip part and has a ring 24 through which the thumb can be passed.

A movable grip part 26 is mounted on the first grip part 22.

This movable grip part 26 is likewise designed as a scissor grip part and has a ring through which a finger can be passed, for example the index finger or middle finger.

The movable grip part 26 is connected pivotably to the first grip part 22 with the aid of a pivot hinge 30 so that it can turn about an axis extending perpendicular to the plane of the grip parts 22, 26.

A lever 32 is additionally mounted between the first grip part 22 and the movable grip part 26. This lever 32 is at one end connected in an articulated manner to the movable grip part 26 about an axis extending perpendicular to the plane of the grip parts 22, 26. At the other end of the lever 32, the latter is connected to a slide 34 which is arranged displaceably in the first grip part 22. The connection between the lever 32 and the slide 34 is likewise designed as a pivot hinge.

The proximal end of the force transmission element 16 is shaped as a hook 36 and engages in the slide 34. The movable grip part 26, the lever 32 and the slide 34 are thus connected to the force transmission element 16 in force-locking manner.

The first grip part 22 also comprises a grub screw 38 which extends through a bore in the first grip part 22. By releasing the grub screw 38 and disengaging the hook 36 from the slide 34, the shaft 12 can thus be removed from the first grip part 22 and from the second grip part 26 connected thereto. This makes cleaning and sterilizing of the instrument easier.

In the area of the hook 36, the shaft 12 also has a seal 40. The proximal end of the force transmission element 16 passes flush through the bore of the seal 40.

The seal 40 prevents escape of liquid, for example an irrigation liquid, at the proximal end of the shaft 12.

In the proximal area of the shaft 12, the latter also has an attachment piece 42 for an irrigation attachment. This attachment can be used to attach an irrigation tube for introducing irrigation liquid into the shaft, which liquid, because of the triangle-shaped cross section of the force transmission element, can be conveyed to the distal end of the shaft, where it can then exit into the operating site.

In the proximal area, the shaft 12 also has a curve 44.

The force transmission element 16 is flattened in the area of this curve 44 in order to permit force transmission about this bend with said force transmission element 16.

At its distal end, the force transmission element 16 has a stop 48 which, upon closure of the tools 18, 20, limits their axial relative movement.

The function of the instrument 10 is described in more detail below.

When the movable grip part 26 is pivoted in the direction of the arrow 50, the lever 32 moves the slide 34 in the direction of the ring 24, that is to say in the direction of the arrow 53. In this way, a force is exerted on the force transmission element 16, and this force likewise acts in the direction of the arrow 52. With the aid of the flattened portion 46, this force is transmitted via the bend 44 of the shaft 12 to the movable tool 18. In this way, the movable tool 18 is drawn axially in the proximal direction, that is to say in the direction of the arrow 54, and the tools 18, 20 are thus closed in order to perform the cutting or punching procedure.

Figure 2:
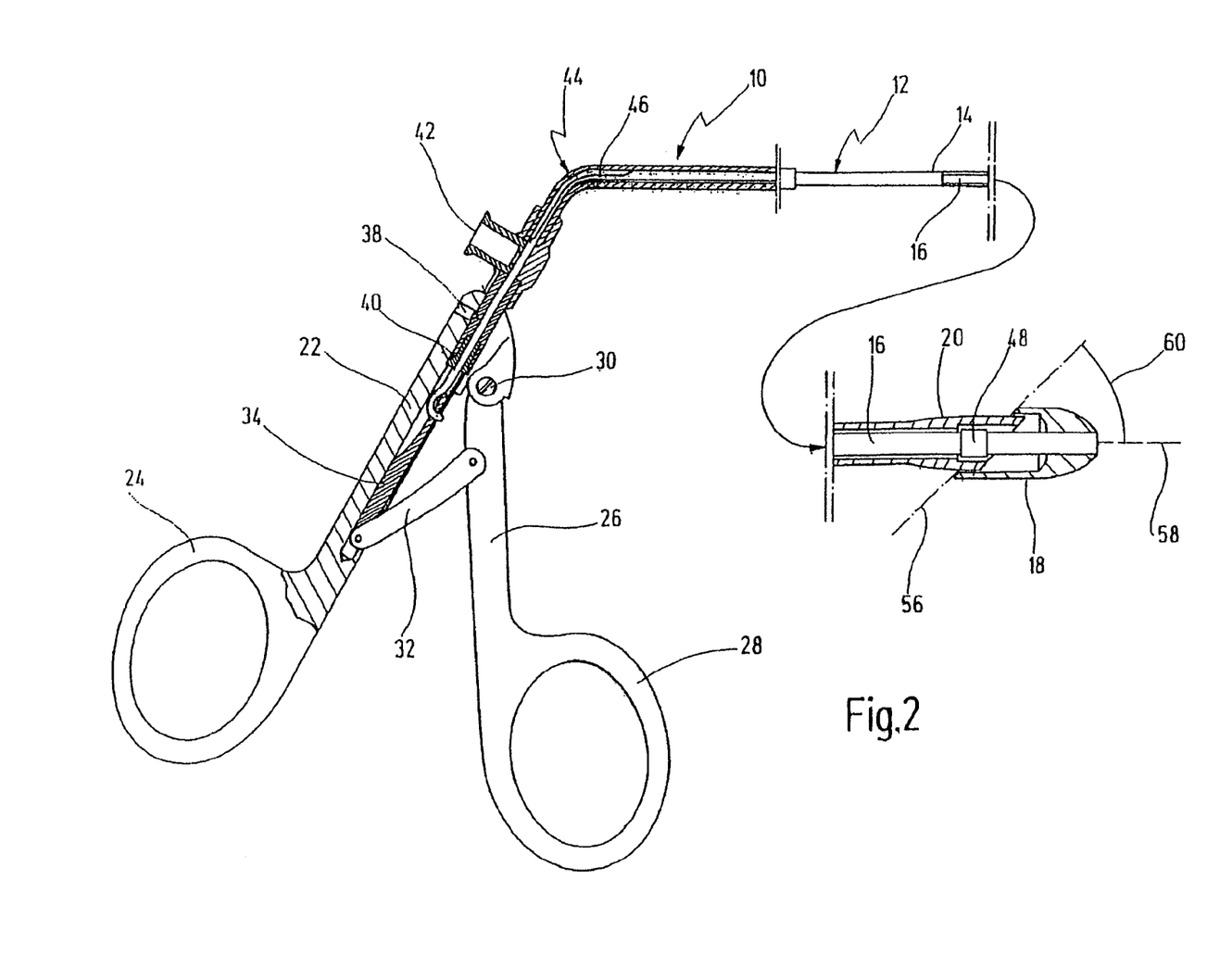
FIG. 2 shows, in a partially sectioned side view, the medical instrument from FIG. 1 with the tools in the closed position, said tools being shown enlarged.

FIG. 2 shows the medical instrument 10 following the movement indicated in FIG. 1, i.e. with the tools 18, 20 closed. It will be seen here that the movable grip part 26 has been moved toward the first grip part 22, as a result of which both the lever 32 and the slide 34 have been moved toward the ring 24. This movement has been transmitted to the first tool 18 via the force transmission element 16, as a result of which said tool 18 has been moved toward the second tool 20. The tools are thus located in the closed position.

It will be seen here how the stop 48 abuts against a shoulder in the second tool 20.

In this drawing, the plane 56 defined by the punch area is also indicated as a dot-and-dash line. The plane 56 is here orthogonal with respect to the plane of the drawing. An angle 60 between the plane 56 and the longitudinal axis 58 of the shaft 12 in the distal portion thereof is approximately 45°.

Figure 3:
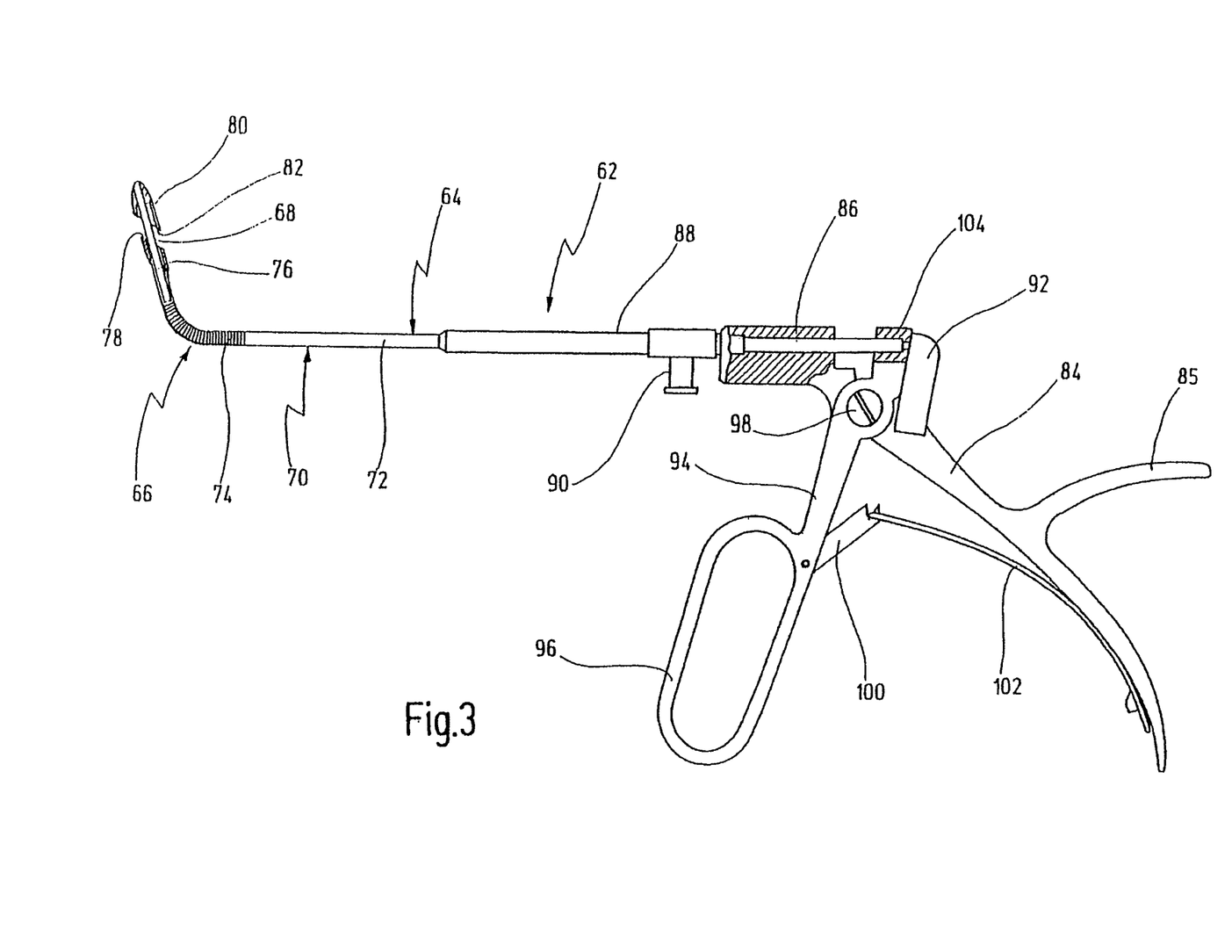
FIG. 3 shows, in a partially sectioned side view, a further illustrative embodiment of a medical instrument according to the invention, with the tools in the open position.

In FIG. 3, a second illustrative embodiment of a medical instrument is designated generally by reference number 62.

The instrument 62 has a shaft 64 which has a curve 66 in a distal portion.

The shaft 64 is designed at least partially as a rod 68 which, in this illustrative embodiment, is of a solid configuration. The shaft 64 also comprises a force transmission element 70 which is designed as a tube 72 in the proximal area and as a helical spring 74 in the area of the curve 66. The helical spring 74 and the tube 72 are connected fixedly to one another.

In the distal direction from the helical spring 74, a first tool 76 is mounted on the force transmission element 70, said first tool 76 being axially movable relative to the shaft 64. A cutting element 78 is mounted at the distal end of the first tool 76. In the distal direction from the first tool 76, a second tool 80 is mounted which has a cutting element 82 at its proximal end. The second tool 80 is here connected fixedly to the rod 68.

The first tool 76 and the second tool 80 are in this case arranged in such a way that, upon an axial movement of the first tool 76 in the direction of the second tool 80, the cutting element 78 extends along the inside of the cutting element 82, with the cutting element 78 of the first tool 76 engaging into the second tool 80.

A first grip part 84 is arranged at the proximal end of the shaft 64.

This grip part 84 has a projection 85 which, during use of the instrument 62 lies in the hollow between thumb and index finger and supports the grip part there during use.

At its upper end, the first grip part 84 has a tubular element 86 which is connected immovably to the grip part.

The tube 72 and the rod 68 each extend movably through the bore of the tubular element 86 in the axial direction.

In the distal direction, the tubular element 86 is continued axially to the shaft 64 by a tubular element 88. The tube 72 and the rod 68 likewise extend movably through the tubular element 88. An attachment piece 90 for an irrigation attachment is mounted at the proximal end of the tubular element 88. Irrigation liquid can thus be introduced between the rod 68 and the tube 72.

A holder 92 is arranged at the proximal end of the shaft 64 and is connected immovably to the rod 68. This holder 92 is likewise connected immovably to the first grip part 84.

A second grip part 94 is moreover connected to the first grip part 84, said second grip part 94 having a long ring 96 through which one, two or three fingers can be passed for operating the instrument 62.

The two grip elements 84 and 94 are connected to one another in an articulated manner via a pivot hinge 98 about an axis extending perpendicular to the plane of the grip parts 84, 92.

The movable grip part 94 also comprises a lever 100 which interacts with a leaf spring 102 mounted on the immovable grip part 84. The lever 100 and the leaf spring 102 cooperate in such a way that the tools 76 and 80 are held in the open position when no force is exerted on the instrument 62.

At its upper end, the movable grip part 94 has a rider 104. This rider 104 is connected immovably to the tube 70. The rod 68 extends movably through the rider 104.

The function of the instrument 62 is described in more detail below.

When the movable grip part 94 is moved toward the first grip part 84, the rider 104 is moved away from the holder 92. In this way, the tube 72, the helical spring 74 and, connected to it, the first tool 78 are moved axially in the distal direction. At the same time, the rod 68 and, connected to it, the second tool 80 are held back by the holder 92 on the first grip part 84. By means of this movement, the tools are closed and the cutting/punching procedure performed.

Figure 4:
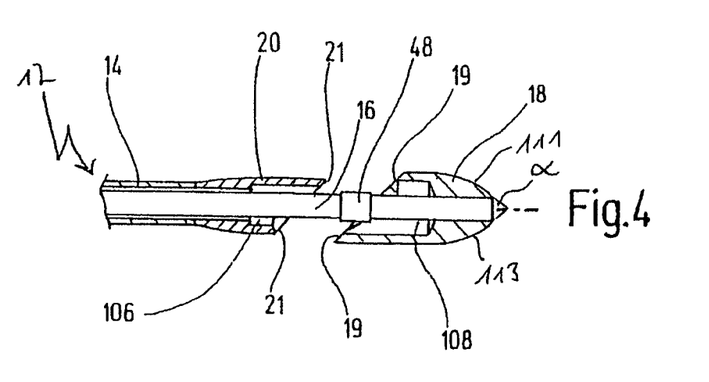
FIG. 4 shows, in a partially sectioned side view, an enlarged representation of the tools of the instrument from FIG. 1.
Figure 5:
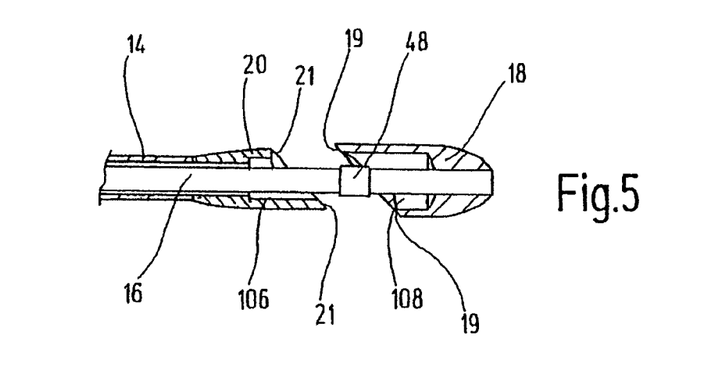
FIG. 5 shows, in a partially sectioned side view, an enlarged representation of the tools of the instrument from FIG. 2.

FIGS. 4 and 5 show an enlarged view of the distal portion or tools 18, 20 of the instruments 10 and 62, respectively. The views differ in that, in FIG. 4, the plane 56 defined by the punch area extends from top-distal to bottom-proximal, whereas in FIG. 5 the plane 56 defined by the punch area extends from top-proximal to bottom-distal.

FIG. 4 also shows that the diameter of the distally arranged tool 18 tapers convexly toward the distal end in the longitudinal direction of the shaft 12, specifically in such a way that the external contour lines of the distally arranged tool, when viewed in a section through a longitudinal central plane, intersect at the distal end at an angle $\alpha$ of smaller than 160° and greater than 50°. The angle $\alpha$ is approximately 85° in the tool 18 in FIG. 4. However, the distally arranged tool 18 does not end in a point. Instead, before the external contour lines 111 and 113 intersect, the distal end of the tool 18 is cut off perpendicular to the longitudinal axis of the shaft 12. Because of the miniaturized configuration of the distally arranged tool 18 with a diameter of less than 3 mm, the distal end of the tool 18 is still relatively pointed.

It will also be seen that the movable tool 18 has a hollow space 106 which serves to enclose cut off tissue and bone pieces, so that these can thus be removed from the operating site.

The second tool 20 likewise has a hollow space 108. This hollow space 108 serves to accommodate the stop 48 which limits the axial relative movement of the tools 18, 20 with respect to one another.

These views also show also show the overall lobe-shaped or paraboloid-shaped profile of the tools 18 and 20.

Figure 10:
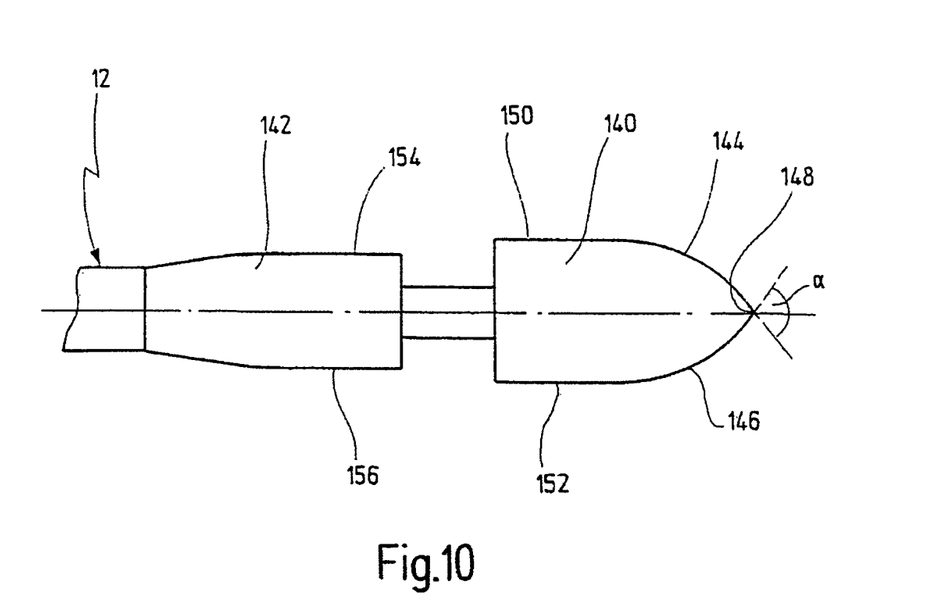
FIG. 10 shows, in an enlarged side view, another illustrative embodiment of tools which can be used in the instrument of FIG. 1 or of FIG. 2 instead of the tools shown there.
Figure 11:
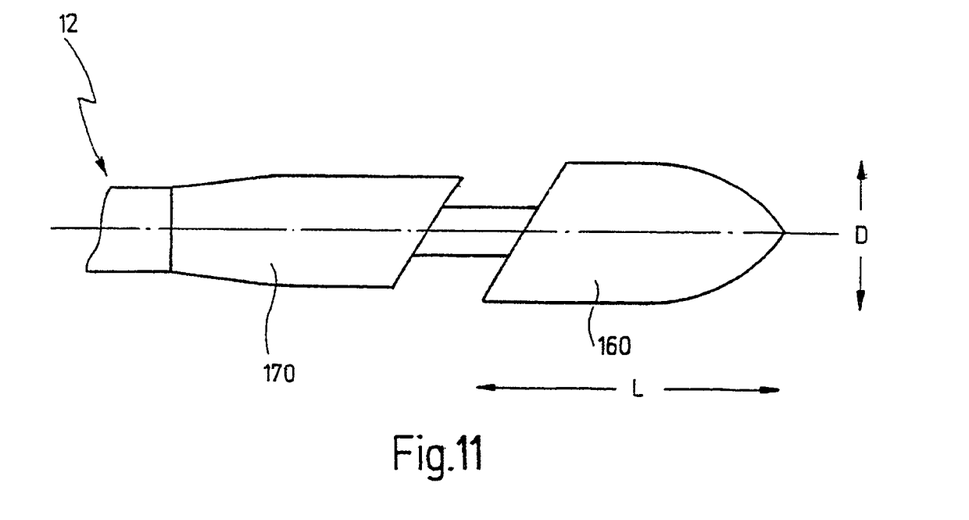
FIG. 11 shows, in an enlarged side view, another illustrative embodiment of tools for use in the instrument from FIG. 1 or in the instrument from FIG. 2.

FIGS. 10 and 11 show further illustrative embodiments of tools which can be used instead of the tools 18, 20 and 76, 80 in the instruments 10 or 62.

FIG. 10 shows a first, distally arranged tool 140 and a second, proximally arranged tool 142 differing from the preceding illustrative embodiments in terms of the following features. The distally arranged tool 140 has a portion tapering convexly toward the distal end in the longitudinal direction of the shaft 12, only part of which is shown in FIG. 10. External contour lines 144 and 146 of this convex portion again intersect at an angle α which is smaller than 160° and greater than 50°, the angle α in FIG. 10 being approximately 120°. In contrast to the tool 18, the external contour lines 144, 146 of the tool 140 run to a distal point 148 which, if appropriate, can be rounded with a very small radius, for example from approximately 0.1 to 0.5 mm, and with which the tool 140 can be placed with spot precision on a bone lamella to be punctured or on a tissue to be punctured.

The convex portion of the tool 140 is adjoined by a straight portion which extends parallel to the longitudinal axis of the shaft 12 and whose external contour lines 150, 152 thus extend rectilinearly. The proximally arranged tool 142 accordingly has, at its distal end, a straight portion with straight external contours 154, 156, and it has a slightly smaller external diameter than the internal diameter of the proximal area of the tool 140, with the result that, during punching, the proximally arranged tool 142 can engage in the distally arranged tool 140 by means of an axial relative movement with respect to said distally arranged tool 140, in order to detach tissue.

The tools 160 and 170 shown in FIG. 11 correspond to the tools 140 and 142, except that the tools 160 and 170 form a punch area which, instead of being perpendicular to the longitudinal axis of the shaft 12, is at an inclination thereto, as has already been described in detail above.

The length L of the distally arranged tool 160 (the same applies to the tool 140 in FIG. 10) is dimensioned in a range of approximately 0.7 to 3 times the diameter D of the tool 160 or 140, respectively.

Figure 6:
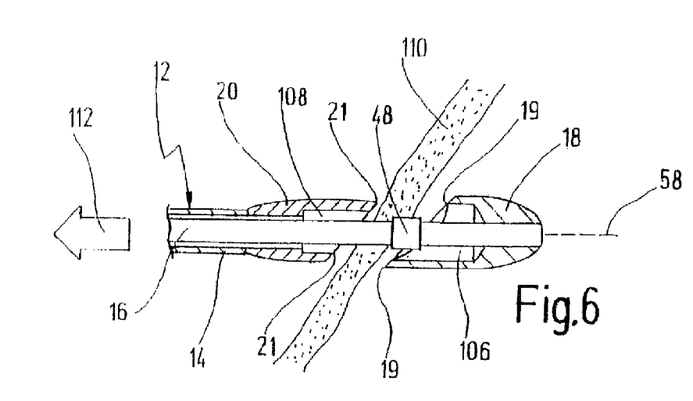
FIG. 6 shows an enlarged representation of the tools of the instrument from FIG. 1 during cutting of a bone lamella.
Figure 7:
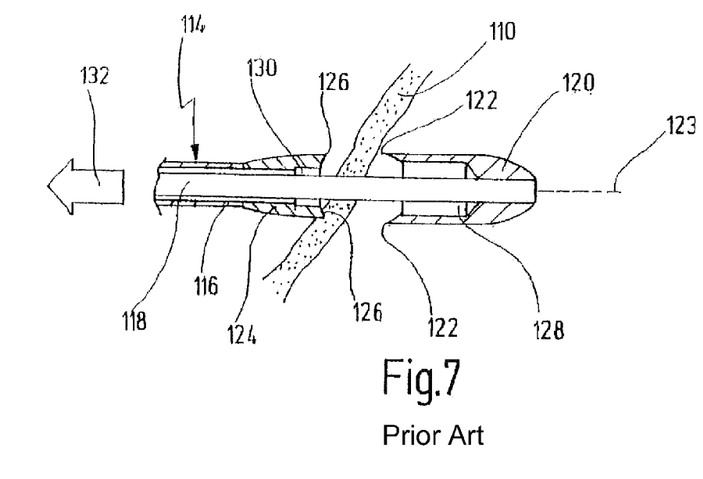
FIG. 7 shows an enlarged representation of the tools of a medical instrument according to the prior art during cutting of a bone lamella.
Figure 8:
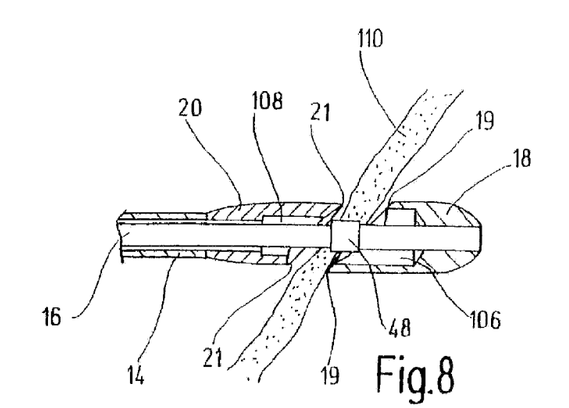
FIG. 8 shows the same representation as in FIG. 6, the tools bearing on the bone lamella prior to cutting.
Figure 9:
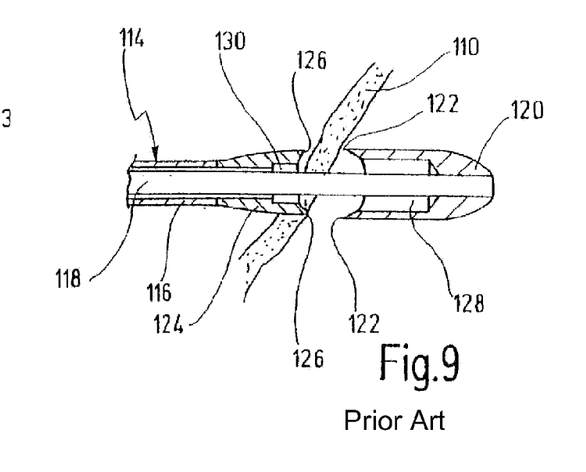
FIG. 9 shows the same representation as in FIG. 7, the tools bearing on the bone lamella prior to cutting.

FIGS. 6 to 9 show the cutting of a bone lamella with the instrument 10 (FIGS. 6 and 8) and an instrument according to the prior art (FIGS. 7 and 9).

FIG. 6 shows the distal portion of the instrument 10 on an enlarged scale corresponding to the view in FIG. 4, the instrument 10 having been moved toward a bone lamella 110 which lies approximately at an angle of 60° to the longitudinal axis 58 of the shaft 12.

FIG. 7 shows the distal portion of a medical instrument according to the prior art, which once again has been moved toward the bone lamella 110. This instrument according to the prior art has a shaft 114 formed by a sleeve-shaped element 116 in which a force transmission element 118 extends movably. At its distal end, the force transmission element 118 has a first tool 120 which has an approximately circular cutting element 122 at its proximal end.

It will be clearly seen here that the sectioning plane defined by the cutting element 122 is perpendicular to the longitudinal axis 123 of the shaft 114. In the proximal direction from the first tool 120, there is a second tool 124 with a cutting element 126 at its distal end. The two tools 120 and 124 each have, in their insides, hollow spaces 128 and 130 for receiving detached pieces of hard tissue or bone. The bone lamella 110 is again at an angle of approximately 60° to the longitudinal axis 123 of the shaft 114.

By a displacement of the respective force transmission element 16, 118 in the proximal direction—in the direction of the arrows 131 and 132 respectively—the respective first axially movable tools 18 and 120 are moved in the direction of the respective second tools 20 and 124, and the tools 18, 20, 120 and 124 are closed. The cutting procedure is represented in each of FIGS. 8 and 9. The first tools 18 and 120 have been moved axially toward the respective second tools 20 and 124, and the respective cutting elements 19, 21 and 122, 126 act on the bone lamella 110.

It will be clear from this that, in the instrument 10, the contact surface of the cutting elements 21 and 19 on the bone lamella is greater than in the instrument according to the prior art, as is shown in FIG. 9. This smaller contact surface in the instrument according to the prior art often leads to breaking off of metal pieces, e.g. from the cutting element 122, which is avoided in the instrument 10.

What is claimed is:

1. A medical instrument for dissecting tissue, comprising a shaft having a longitudinal axis and a distal end,
   a first tool and a second tool both arranged at said distal end of said shaft, said first tool being arranged distally from said second tool,
   said first and second tools cooperating in the manner of a punch by an axial relative movement with respect to one another,
   at least one of said first and second tools comprising a cutting element arranged in such a way that said cutting element forms a punch area with the other of said first and second tools, said punch area defining a plane which forms a first angle with said longitudinal axis of said shaft which is different than 0° and which is different than 90° in the area of said distal end of said shaft,
   said distally arranged first tool tapering in diameter convexly in distal direction, external contour lines of said distally arranged first tool intersecting, when viewed in a section through a longitudinal central plane, at a second angle smaller than 160°; and
   wherein said second tool which is proximally arranged with respect to the distally arranged first tool has a smaller external diameter than a proximal end of said distally arranged first tool such that said proximally arranged second tool engages inside of the diameter of said distally arranged first tool during punching.

2. The instrument of claim 1, wherein said second angle is smaller than 140°.

3. The instrument of claim 1, wherein said second angle is smaller than 120°.

4. The instrument of claim 1, wherein said second angle is smaller than 100°.

5. The instrument of claim 1, wherein said external contour lines run together to a point.

6. The instrument of claim 1, wherein said convex distal portion of said distally arranged first tool merges at least approximately into a straight portion extending parallel to said longitudinal axis of said shaft.

7. The instrument of claim 1, wherein said first angle is in the range from approximately 20° to approximately 80°.

8. The instrument of claim 1, wherein said first angle is in the range of approximately 30° to approximately 70°.

9. The instrument of claim 1, wherein said plane defined by said punch area extends from top-proximal to bottom-distal.

10. The instrument of claim 1, wherein said plane defined by said punch area extends from top-distal to bottom-proximal.

11. The instrument of claim 1, wherein said plane defined by said punch area extends from right-proximal to left-distal.

12. The instrument of claim wherein said plane defined by said punch area extends from right-distal to left-proximal.

13. The instrument of claim 1, wherein said cutting element is designed about a complete circumference on at least one of said first tool and said second tool.

14. The instrument of claim 1, wherein said first and second tools have an approximately circular cross section.

15. The instrument of claim 14, wherein a diameter of said first and second tools is in the range of approximately 2 to approximately 8 mm.

16. The instrument of claim 15, wherein said diameter of said first and second tools is in the range of approximately 3 mm to approximately 5 mm.

17. The instrument of claim 1, wherein said first tool and said second tool form, in a closed position of said first and second tools, a profile chosen from the group comprising a ball-shaped profile, a double paraboloid profile, an ellipsoid profile, a tear-shaped profile, a lobe-shaped profile.

18. The instrument of claim 1, wherein said distally arranged first tool is immovable and said second tool is movable.

19. The instrument of claim 1, wherein said first tool and said second tool are secured against turning relative to one another.

20. The instrument of claim 1, wherein said first and second tools both have cutting elements.

21. The instrument of claim 1, wherein said shaft is straight.

22. The instrument of claim 1, wherein said shaft has at least one curve.

23. The instrument of claim 22, wherein an angle of curvature of said curve is in the range of approximately 20° to approximately 90°.

24. The instrument of claim 22, wherein an angle of curvature of said curve is in the range of approximately 45° to approximately 65°.

* * * * *